United States Patent
Daniel et al.

(10) Patent No.: US 9,212,117 B2
(45) Date of Patent: Dec. 15, 2015

(54) PROCESS FOR PRODUCING ACETIC ACID AND DIMETHYL ETHER USING A ZEOLITE CATALYST

(75) Inventors: Berian John Daniel, Beverley (GB); David John Law, Beverley (GB); John Glenn Sunley, Cottingham (GB)

(73) Assignee: BP CHEMICALS LIMITED, Middlesex (GB)

( * ) Notice: Subject to any disclaimer, the term of this patent is extended or adjusted under 35 U.S.C. 154(b) by 963 days.

(21) Appl. No.: 13/392,551

(22) PCT Filed: Aug. 31, 2010

(86) PCT No.: PCT/GB2010/001648
§ 371 (c)(1),
(2), (4) Date: Feb. 27, 2012

(87) PCT Pub. No.: WO2011/027105
PCT Pub. Date: Mar. 10, 2011

(65) Prior Publication Data
US 2012/0165570 A1    Jun. 28, 2012

(30) Foreign Application Priority Data
Sep. 3, 2009    (EP) .................................. 09252123

(51) Int. Cl.
C07C 53/08    (2006.01)
C07C 51/09    (2006.01)
C07C 41/09    (2006.01)
C07C 43/04    (2006.01)

(52) U.S. Cl.
CPC ................. C07C 41/09 (2013.01); C07C 51/09 (2013.01)

(58) Field of Classification Search
CPC ........ C07C 41/09; C07C 51/09; C07C 43/04; C07C 53/08

USPC ......................................................... 562/607
See application file for complete search history.

(56) References Cited

U.S. PATENT DOCUMENTS

| 5,235,102 A | 8/1993 | Palmer et al. |
| 5,684,213 A | 11/1997 | Nemphos et al. |
| 6,521,783 B1 | 2/2003 | Wegman et al. |
| 8,809,573 B2 * | 8/2014 | Armitage et al. ............. 560/232 |

FOREIGN PATENT DOCUMENTS

| DE | 36 06 169 A1 | 8/1987 |
| EP | 1 396 483 A1 | 3/2004 |
| WO | WO 2004/074228 A1 | 9/2004 |
| WO | WO 2006/041253 A1 | 4/2006 |
| WO | WO2009/077720 A1 * | 6/2009 |

OTHER PUBLICATIONS

Hoelderich et al. "Process for preparing acetic acid, methyl acetate and/or dimethyl ether" DE 3606169 A1 (pub. Aug. 27, 1987) English Machine Translation.*
Baerlocher, C.; McCusker, L. B.; and Olso, D. H. Atlas of Zeolite Framework Types, 6th Ed. Amsterdam: Elsevier Science, 2007 (p. 214-215).*
PCT International Preliminary Report on Patentability, mailed Mar. 15, 2012; PCT International Application No. PCT/GB2010/001648, filed Aug. 31, 2010 (8 pgs).

* cited by examiner

*Primary Examiner* — Joseph Kosack
*Assistant Examiner* — Amanda L Aguirre
(74) *Attorney, Agent, or Firm* — Nixon & Vanderhye P.C.

(57) ABSTRACT

Process for the production of acetic acid and dimethyl ether by contacting methanol and methyl acetate with a catalyst composition at a temperature in the range 140 to 250 ° C. The catalyst composition contains a zeolite having a 2-dimensional channel system comprising at least one channel which has a 10-membered ring.

21 Claims, No Drawings

PROCESS FOR PRODUCING ACETIC ACID AND DIMETHYL ETHER USING A ZEOLITE CATALYST

This application is the U.S. national phase of International Application No. PCT/GB2010/001648 filed 31 Aug. 2010 which designated the U.S. and claims priority to European Application No. 09252123.6 filed 3 Sep. 2009, the entire contents of each of which are hereby incorporated by reference.

The present invention relates to a process for the production of acetic acid and dimethyl ether from a feedstock comprising methanol and methyl acetate in the presence of a zeolite catalyst.

The most widely used industrial process for production of acetic acid is the carbonylation of methanol, which is described generally, for example, in British patents 1,185,453 and 1,277,242 and U.S. Pat. No. 3,689,533. In that type of process, methanol is reacted with carbon monoxide in the presence of a rhodium- or iridium-containing catalyst, in the additional presence of a halogen (usually iodine)-containing promoter.

Dimethyl ether can be produced, for example, by direct synthesis from a synthesis gas prepared by reforming hydrocarbon materials such as methane, or by the dehydration of methanol. Among these, processes for producing dimethyl ether by the dehydration of methanol is described, for example in EP 1396483, U.S. Pat. No. 5,684,213, WO 2004/074228 and WO 2006/041253.

Typically, industrial processes for the dehydration of methanol to dimethyl ether employ alumina catalysts, and are carried out at high temperatures, typically at temperatures in excess of 250° C. High temperatures are desirable in order to achieve commercially acceptable rates of reaction. For example, in EP-A-1396483 there is described a process for producing dimethyl ether by dehydrating methanol in the vapour phase in the presence of an activated alumina catalyst at temperatures, disclosed as being, preferably in excess of 250° C., more preferably 280° C. or more in the light of a reaction rate.

It is also known, that dialkyl ethers may be produced by dehydrating alcohols under catalytic distillation conditions. For example, there is described in U.S. Pat. No. 5,684,213, a process for producing dialkyl ethers, including dimethyl ether, by the dehydration of the corresponding alcohol in the presence of hydrogen in a distillation column reactor. The catalyst is said to be a zeolite and where the dialkyl ether is dimethyl ether, the preferred zeolite is mordenite.

However, a disadvantage associated with dehydration methods used for producing dimethyl ether from methanol in the presence of alumina or zeolite catalysts is that at the reaction temperatures employed (typically in excess of 250° C.), hydrocarbons are usually co-produced together with the targeted dimethyl ether product, and then form coke on the catalyst surface which deactivates the catalyst and hence reduces the reaction rate.

It is suggested in "Effect of γ-alumina content on catalytic performance of modified ZSM-5 for dehydration of crude methanol to dimethyl ether" Shin Dong Kim et al. Applied Catalysis A: General 309 (2006) 139-143, that a method of reducing hydrocarbon formation at 270° C. is to modify the ZSM-5 by exchange with sodium.

WO 2004/074228 describes a process for preparing dimethyl ether in high yield by employing a dual-charged catalyst system. Methanol is initially dehydrated over a hydrophilic solid acid catalyst, such as γ-alumina; unreacted methanol is then dehydrated over a hydrophobic zeolite catalyst, such as ZSM-5.

A further disadvantage of the use of γ-alumina to catalyse the dehydration of methanol, is that γ-alumina is hydrophilic and thus methanol feedstock is required to be virtually anhydrous in order to avoid catalyst deactivation.

WO 2006/041253 describes a process for preparing dimethyl ether from methanol containing water by firstly contacting the methanol with a partially substituted hydrophobic zeolite, such as Na-ZSM-5, followed by contacting with a catalyst selected from γ-alumina or silica-alumina. The dehydration is conducted in an adiabatic reactor instead of a conventional isothermal reactor.

In the presence of water, methyl acetate is hydrolysed to acetic acid and methanol. For example, there is described in U.S. Pat. No. 5,235,102 a catalytic distillation process for the hydrolysis of methyl acetate to produce acetic acid. The catalyst for use in this process is said to be a catalyst-packing material comprising a rigid, cellular monolith, such as cordierite and mullite.

It is also known from CN 1541991 that esters may be hydrolysed to the corresponding acid in the presence of an ammonium salt of a heteropolyacid, such as an ammonium salt of a phosphotungstic acid or a silicotungstic acid.

Polymeric resins, such as those based on styrene divinylbenzene copolymers with sulphonic acid groups, for example, Amberlyst™36WET (bead form macroreticular sulfonic acid ion exchange resin avalilable from the Rohm&Haas Company) can also be used to catalyse the hydrolysis of methyl acetate to acetic acid. Typically, however, such resins have a maximum operating temperature of about 150°C.

In an embodiment of U.S. Pat. No. 6,521,783 there is described a process in which acetic acid, methyl acetate, methanol, dimethyl ether and water is fed to a hydrolysis/dehydration reactor which contains an ester hydrolysis catalyst and an alcohol dehydration catalyst which can be the same or different. The alcohol dehydration catalyst can be selected from a solid acid, heteropolyacids, acidic zeolites, titania or silica promoted alumina, aluminium phosphate or tungsten oxide supported on silica-alumina. The ester hydrolysis catalyst can be selected from acidic ion-exchange resins, acidic gamma alumina, fluorinated alumina, sulphate or tungstate promoted zirconia, titania or silica promoted alumina, aluminium phosphate, tungsten oxide supported on silica-alumina, clays, supported mineral acids, zeolites or heteropolyacids. In an example relating to this process, the reaction is carried out at 300° C. at 200 psia. The catalyst is not identified.

It has now been found that the process efficiency of a combined methanol dehydration and methyl acetate hydrolysis reaction can be improved significantly by the use of a zeolite which has a 2-dimensional channel system comprising at least one channel having a 10-membered ring.

Accordingly, the present invention provides a process for the production of acetic acid and dimethyl ether in which process methanol and methyl acetate are contacted with a catalyst composition in a reaction zone at a temperature in the range 140 to 250° C. to produce acetic acid and dimethyl ether wherein said catalyst composition comprises a zeolite which has a 2-dimensional channel system comprising at least one channel having a 10-membered ring.

A feature of the invention is that a zeolite which has a 2-dimensional channel system comprising at least one channel having a 10-membered ring is employed in the catalyst for use in the process. Surprisingly, it has been found that the use of zeolites having a 2-dimensional channel system comprising at least one channel having a 10-membered ring enhances the space time yields (STY's) of the products. Furthermore, enhanced space time yields are achieved at lower temperatures than typically used for the dehydration of methanol, with only low levels of by-product formation and without the need to reduce the acidity of the zeolite, for example, by exchange with metal ions.

In the process of the present invention acetic acid and dimethyl ether are produced by the dehydration and hydrolysis of a feedstock comprising methanol and methyl acetate. The methanol dehydration and methyl acetate hydrolysis reactions can be represented by equations (1) and (2) respectively:

$$2CH_3OH \leftrightharpoons CH_3OCH_3 + H_2O \quad (1)$$

$$CH_3COOCH_3 + H_2O \leftrightharpoons CH_3COOH + CH_3OH \quad (2)$$

The dehydration and hydrolysis reactions are catalysed by a zeolite which has a 2-dimensional channel system comprising at least one channel having a 10-membered ring.

Channel systems in zeolites are described as being 0-, 1-, 2- or 3-dimensional. However, the zeolites found to be useful in the process of the present invention possess a 2-dimensional channel system. The 2-dimensional channel system can comprise interconnecting channels. Alternatively, the 2-dimensional channel system can comprise channels which are non-interconnecting.

The channel systems of a zeolite may possess rings having, for example, 4, 5, 6, 8, 10, 12, 14 or 16 members. The 2-dimensional channel system of the zeolite for use in the process of the present invention has at least one channel which has a 10-membered ring.

Examples of zeolites suitable for use in the process of the present invention are zeolites having framework structure types, FER (typified by ferrierite and ZSM-35), HEU (typified by Clinoptilolite), DAC (dachiardite), MFS (for example ZSM-57), STI (for example, stilbite), NES (for example, NU-87), MWW (for example, MCM-22) and TER (terranovaite). The three-letter codes such as 'FER' refer to the framework structure type of the zeolites using the nomenclature proposed by the International Zeolite Association. Information about structure codes and zeolites is available on the website of the International Zeolite Association at www.iza-online.org.

Preferably, the zeolite for use in the present invention further comprises at least one channel having an eight-membered ring. Examples of such zeolites are those having framework structure types FER (such as ferrierite and ZSM-35), HEU (such as clinoptilolite), MFS (such as ZSM-57), DAC (dachiardite) and STI (such as stilbite).

Particularly preferred zeolites are those of framework structure type FER, HEU or MFS.

For the purposes of the present invention, it is preferred that the zeolites are acidic. Suitably, the zeolite is used, at least partially, preferably practically entirely in the acid form generally referred to as the 'H' form of the zeolite. Other forms of the zeolite, such as the $NH_4$ form can be converted to the H-form, for example, by calcining the $NH_4$ form at elevated temperature. The acid form of a zeolite will possess Brønsted acid ($H^+$) sites which are distributed among the various channel systems in the zeolite. The number or concentration of $H^+$ species residing in any particular channel system can be determined by known techniques such as infra-red spectroscopy. The degree of acidity of the zeolite can be influenced by the exchange of H+ sites by, for example, by metal ions such as the alkali metals, sodium and potassium. The greater the extent of exchange by the alkali metal, the lower the acidity of the zeolite. Preferably, zeolites for use in the present invention contain only trace amounts of alkali or alkaline earth metals. Suitably, the amount of alkali and alkaline earth metals present in a zeolite is such that the zeolite retains at least 90% of its Brønsted acid ($H^+$) sites. For use in the present invention, the total amount of alkali and alkaline earth metals present in the zeolite is suitably in the range 0 to 0.2% by weight of the zeolite.

Preferred zeolites for use in this invention are aluminosilicate zeolites. The silica:alumina ratio of a zeolite is preferably in the range 5 to 200:1. If the silica:alumina ratio of a zeolite exceeds 200, the amount of its acid sites becomes negligible and its efficiency to catalyse the methanol dehydration will be impaired. Thus, the silica:alumina ratio of a zeolite is more preferably in the range 5 to 90:1, especially, 15 to 60:1.

Synthetic zeolites are typically prepared in the form of powders. Since a powder has no significant mechanical strength, its practical applications are limited. Mechanical strength can be conferred on a zeolite by forming a zeolite aggregate, for example, a shaped body, such as a pill or extrudate. An extrudate may be formed by extruding the zeolite in the presence of a binder and drying and calcining the resulting extrudate.

In addition to the zeolite, the catalyst composition preferably comprises at least one inorganic oxide binder. Examples of suitable inorganic oxide binders are silicas, aluminas, alumina-silicates, magnesium silicates, magnesium aluminium silicates, titanias, zirconias and clays, especially alumina, alumina-silicate or silica binders. Examples of suitable aluminas include boehemite type alumina and gamma alumina.

Suitably, the inorganic oxide binder may be present in the catalyst composition in an amount in the range of 10 wt % to 90 wt %, preferably, in the range of 15 wt % to 60 wt % (based on total weight of zeolite and binder).

According to the present invention, the feedstock that is used as the starting material for the production of acetic acid and dimethyl ether comprises a mixture of methanol and methyl acetate.

The methanol and methyl acetate may be fed to the reaction zone as separate feed streams or as a single feed stream.

The methanol and methyl acetate may be fed to the reaction zone in any desired ratio but suitably, the molar ratio of methanol:methyl acetate is in the range 1:0.1 to 1:10, such as 1:1 to 1:10, preferably 1:0.2 to 1:5.

The hydrolysis reaction requires water as a reactant. Water may be obtained from the dehydration reaction, which produces water in-situ. Preferably, however, water is added to the reaction zone. The amount of added water should not be so high as to substantially reduce catalytic activity. Suitably, water may added in an amount in the range 0.1 to 50 mol %, preferably in the range 3 to 40 mol % and, more preferably in the range 5 to 30 mol % based on total feed of methyl acetate, methanol and water.

The methanol and/or methyl acetate feed streams to the reaction zone may optionally comprise other components. Such components can include one or more of acetic acid, dimethyl ether and water.

A diluent such as an inert gas, for example, nitrogen and helium may also be fed to the reaction zone.

The process may be carried out as a vapour phase or as a liquid phase process, for example, as a fixed bed process or a slurry phase process.

Where the process is operated as a vapour phase process, the components of the feed stream(s) may, prior to entering the reaction zone, be in the liquid phase. However, prior to contact with the zeolite, the liquid phase components should be volatilised, for example, by use of a pre-heater.

The process is carried out at a temperature in the range 140 to 250° C. Preferably, it is carried out at a temperature in the range 160 to 250° C., such as 170 to 240° C. More preferably, where the process is carried out in the liquid phase, the temperature is in the range 170 to 210° C., such as 170 to 190° C., for example, 170 to 180° C. However, a liquid phase process may also be carried out at temperatures in the range 160 to 190° C. Where the process is carried out in the vapour phase, most preferably, the temperature is in the range 175 to 250° C., such as in the range 175 to 240° C., for example, in the range 175 to 220° C. and in the range 175 to 200° C.

The applicants have unexpectedly found that by operating at these temperature ranges (which are particularly low when compared to the typical temperatures employed in the field), they were not only able to benefit from the usual advantages of operating a process of a reduced temperature, but they also found the catalyst had surprisingly high activity at such low temperatures.

The process may be carried out at atmospheric pressure or at pressures greater than atmospheric. Where the process is carried out in the liquid phase, it is preferred to operate the process at a total reaction pressure which is sufficient to maintain the dimethyl ether product in solution. Suitably, therefore, the pressure may be at least 40 bar, such as 40 to 100 barg, suitably 40 to 60 barg. Where the process is carried out in the vapour phase, suitable operating pressures are in the range atmospheric to 30 barg, such as 10 to 20 barg.

The gas hourly space velocity (GHSV) is suitably in the range 500 to 40,000 $h^{-1}$, such as 2,000 to 25,000 $h^{-1}$, for example 2,000 to 15,000 $h^{-1}$.

The liquid hourly space velocity (LHSV) is suitably in the range 0.2 to 20, such as in the range 0.5 to 10 $h^{-1}$, for example, 0.5 to 5 $h^{-1}$ or in the range 2 to 8 $h^{-1}$.

According to a preferred embodiment of the present invention, the operating conditions under which the process is conducted are maintained such that the process is operated in the vapour phase.

In an embodiment of the process of the present invention, the process is operated in the vapour phase at a temperature in the range 175 to 220° C., water is added to the reaction zone, the zeolite further comprises at least one channel having an 8-membered ring and is in the acid form and, preferably, the gas hourly space velocity (GHSV) is in the range 2 to 25,000 $h^{-1}$.

In a further embodiment of the process of the present invention, the process is operated in the liquid phase at a temperature in the range 160 to 190° C., water is added to the reaction zone and wherein the zeolite further comprises at least one channel having an 8-membered ring and is in the acid form and, preferably, the liquid hourly space velocity (LHSV) is in the range 2 to 8 $h^{-1}$.

The process may be operated as either a continuous or a batch process, preferably as a continuous process.

In the process of the present invention, a product stream comprising acetic acid, dimethyl ether, water, methanol and methyl acetate is produced from the reactant feed stream(s) of methanol, methyl acetate, and optional water. The acetic acid and dimethyl ether may be recovered from the product stream by conventional purification methods, such as by distillation. Dimethyl ether will generally be recovered as an overhead from a distillation column, and the acetic acid will typically be recovered as a bottoms fraction from the column together with methyl acetate, methanol and water. The acetic acid can be separated from these components by further distillation. The recovered dimethyl ether may be used as a feedstock to a process for the production of methyl acetate by the carbonylation of dimethyl ether with carbon monoxide. The acetic acid may be sold or may be used as a feed in other downstream processes, such as the manufacture of vinyl acetate or ethyl acetate.

The invention is now illustrated with reference to the following Examples.

EXAMPLE 1

In this Example, various zeolites were tested for catalytic activity in the production of acetic acid and dimethyl ether from a mixture of methanol and methyl acetate in the liquid phase. The zeolites were tested in their acid form. The experiments were conducted on an X-Cube™ high pressure high temperature continuous flow reactor system (ex ThalesNano Nanotechnology Incorporated) at a temperature of 170° C., a pressure of 50 barg, a liquid hourly space velocity of 4 $hr^{-1}$ and a feed comprising 50 mol% methanol and 50 mol% methyl acetate. Liquid reaction product from the reactor was collected after 50 hours on stream and analysed using a gas chromatograph equipped with a CP-Wax52CB column having FID for oxygenate analysis and also a gas chromatograph equipped with DB-Wax on open tubular silica column with TCD for water analysis. The results of the experiments are given in Table 1 below.

TABLE 1

| Catalyst | Channel System | Ring Size | Framework Type | Dimethyl Ether STY* (g/kg/hr) | Acetic Acid STY (g/kg/hr) | Methanol Conversion (%) |
| --- | --- | --- | --- | --- | --- | --- |
| Ferrierite (SAR 17 + 20 wt % alumina binder) | 2-D | 10, 8 | FER | 1354 | 454 | 81.6 |
| Ferrierite (SAR55) | 2-D | 10, 8 | FER | 1224 | 375 | 68.3 |
| ZSM-35 (SAR 18) | 2-D | 10, 8 | FER | 1063 | 357 | 84.4 |
| Ferrierite (SAR20 + 20 wt % alumina binder) | 2-D | 10, 8 | FER | 1032 | 353 | 76.5 |
| ZSM-5 (SAR23 + 20 wt % alumina binder) | 3-D | 10 | MFI | 922 | 292 | 66.0 |

TABLE 1-continued

| Catalyst | Channel System | Ring Size | Framework Type | Dimethyl Ether STY* (g/kg/hr) | Acetic Acid STY (g/kg/hr) | Methanol Conversion (%) |
|---|---|---|---|---|---|---|
| SUZ-4 (SAR 17) | 3-D | 10, 8 | SZR | 832 | 220 | 60.7 |
| Mordenite (SAR20 + 20 wt % alumina binder) | 1-D | 12, 8 | MOR | 721 | 155 | 50.8 |
| Mordenite (SAR 50 + 20 wt % alumina binder) | 1-D | 12, 8 | MOR | 672 | 151 | 41.6 |
| Zeolite Beta (SAR 20) | 3-D | 12 | BEA | 658 | 161 | 50.7 |
| Zeolite Y (SAR30 + 20 wt % alumina binder) | 3-D | 12 | FAU | 151 | 26 | 17.3 |

SAR = silica:alumina molar ratio. The wt % of binder is the wt % based on total weight of the zeolite and binder.
*Calculated from mols acetic acid + mols water produced

EXAMPLE 2

A number of experiments were carried out to test the catalytic activity of ferrierite and ZSM-5 in the liquid phase production of acetic acid and dimethyl ether from a feed of methanol, methyl acetate and water. The silica:alumina ratios of the ferrierite and ZSM-5 were 20 and 23 respectively. The ZSM-5 contained 20 wt % alumina binder (based on total weight). The experiments were conducted on an X-Cube™ continuous flow reactor (ex ThalesNano Nanotechnology Incorporated). In each experiment the reaction was carried out at a temperature of 170° C., a pressure of 50 barg, a liquid hourly space velocity of 8 hr$^{-1}$ and a feed containing 8.5 mol % methanol, 69.2 mol % methyl acetate and 22.3 mol % water. After approximately 170 hours on stream, the temperature in each experiment was raised to 180° C. and the pressure increased to 70 barg, the liquid hourly space velocity and feed composition were unchanged. Liquid reaction product from the reactor was collected after 50, 100 and approximately 200 hours on stream and analysed using gas chromatographs equipped with an open tubular silica column coated with CP-Poraplot Q and a TCD. The results of the experiments are given in Table 2 below.

The above experiment was repeated using, as catalyst, Amberlyst™ 36WET resin (ex Rohm&Haas Company) except that, owing to the maximum operating temperature of the resin (150° C.) the experiment was carried out at a 140° C. instead of 170° C. The results using Amberlyst™ 36WET are given in Table 2 below.

TABLE 2

| Catalyst | Time on stream (hrs) | Temp. (° C.) | Pressure (barg) | Dimethyl Ether STY (g/l/hr) | Acetic Acid STY (g/l/hr) |
|---|---|---|---|---|---|
| Ferrierite | 50 | 170 | 50 | 236 | 874 |
| | 100 | 170 | 50 | 237 | 876 |
| | 200 | 180 | 70 | 393 | 1083 |
| ZSM-5 | 50 | 170 | 50 | 197 | 861 |
| | 100 | 170 | 50 | 178 | 833 |
| | 171 | 180 | 70 | 356 | 1066 |
| Amberlyst ™ 36 | 50 | 140 | 50 | 49 | 661 |
| | 100 | 140 | 50 | 47 | 658 |

EXAMPLE 3

This experiment was carried out to test ferrierite for catalytic activity in the vapour phase production of acetic acid and dimethyl ether from methanol and methyl acetate. Ferrierite having a silica:alumina ratio of 20 and bound with 20 wt % of alumina (based on total weight) was sieved to a particle size diameter in the range 500 to 1000 microns. 6 ml of the ferrierite diluted with 12 ml of silica and supported on a glass wool plug, was then loaded into a hastelloy tube reactor containing 48 ml of a pre-bed of carborundum. A glass wool plug separated the catalyst and the pre-bed. A vapour phase feed of 25 mol % methyl acetate, 15 mol % methanol, 10 mol % water and 50 mol % helium was introduced into the reactor and contacted the ferrierite catalyst at a temperature of 175° C., a pressure of 10 barg and a gas hourly space velocity of 2790 h$^{-1}$. The reaction was allowed to continue for 190 hours. The gaseous product stream was analysed by gas chromatography. The liquid product stream was collected in a pressurised vessel which was let-down to atmospheric pressure and the contents analysed by gas chromatography. Based on methanol conversion and acetic acid make, the space time yield (STY) to dimethyl ether was found to be 419 g/l/hr; the STY to acetic acid was 216 g/l/hr. The carbon dioxide by-product make was found to be 0.03 g/l/hr. No acetone was detected.

EXAMPLES 4 to 7

Experiments were carried out to test ferrierite for catalytic activity in the production of acetic acid and dimethyl ether from methanol and methyl acetate in the vapour phase using high gas hourly space velocities. 0.7 ml ferrierite (silica:alumina ratio of 20) bound with 20 wt % of alumina (based on total weight) and supported on a glass wool plug, was loaded into a hastelloy U-tube reactor containing 30 ml of a pre-bed of carborundum. A glass wool plug separated the catalyst and pre-bed. The temperature and pressure of the reactor was adjusted to the reaction temperature of 190° C. and a pressure of 10 barg. A vapour phase feed comprising 10 mol % methyl acetate, 6 mol % methanol, 4 mol % water and 80 mol % helium was contacted with the catalyst at a gas hourly space velocity (GHSV) of 7735 h$^{-1}$. The reaction was allowed to continue for 90 hours at 190° C. The temperature was then reduced to 185° C. and the reaction allowed to continue for a further 70 hours. The product stream was analysed on-line at regular intervals using a mass spectrometer and a micro-gas chromatograph. The experiment was then repeated except that the gas hourly space velocity was increased to 10770 h$^{-1}$ and the volume of catalyst was reduced to 0.5 ml.

The results of the experiments are given in Table 3 below.

TABLE 3

| Example | Catalyst | Temp. (° C.) | GHSV (h$^{-1}$) | Dimethyl Ether STY* (g/L/hr) | Acetic Acid STY (g/L/hr) |
|---|---|---|---|---|---|
| 4 | Ferrierite | 190 | 7735 | 494 | 279 |
| 5 | Ferrierite | 185 | 7735 | 471 | 237 |
| 6 | Ferrierite | 190 | 10770 | 661 | 349 |
| 7 | Ferrierite | 185 | 10770 | 621 | 287 |

*data based on (methanol converted + acetic acid produced)/2

EXAMPLE 8

In this Example the catalytic activity of zeolites having channels containing different ring sizes was tested. The zeolites tested were H-ZSM-35, H-SUZ-4 and H-Beta. The silica : alumina ratios of the zeolites were 18, 17 and 20 respectively. Prior to use each zeolite was pressed and sieved to particle sizes in the range 250 to 500 microns.

Example 4 was repeated except that a temperature of 180° C. and a gas hourly space velocity of 7735 h$^{-1}$ was maintained throughout the course of each reaction. The average space time yields (STY) to acetic acid and dimethyl ether for the period 150 to 170 hours on stream are given in Table 4 below.

TABLE 4

| Catalyst | Channel System | Ring Size | Framework Type | Acetic Acid STY (g/l/hr) | Dimethyl Ether STY* (g/l/hr) |
|---|---|---|---|---|---|
| ZSM-35 | 2-D | 10, 8 | FER | 219 | 437 |
| SUZ-4 | 3-D | 10, 8 | SZR | 64 | 244 |
| Beta | 3-D | 12 | BEA | 51 | 86 |

*based on (methanol converted + acetic acid produced)/2

EXAMPLE 9

In this Example, the catalytic activities of H-ferrierite, H-mordenite and H-ZSM-5 were tested. Each zeolite was bound with 20% by weight of alumina (based on total weight). The silica:alumina ratio of each zeolite was approximately 20. Prior to use each zeolite was crushed and sieved to particle sizes in the range 250 to 500 microns.

Example 4 was repeated except that a temperature of 200° C. and a gas hourly space velocity of 7600 h$^{-1}$ were maintained throughout the course of each reaction. The average space time yields (STY) to acetic acid and dimethyl ether in the time interval 220 to 240 hours on stream are given in Table 5 below.

TABLE 5

| Catalyst | Channel System | Ring Size | Acetic Acid STY (g/l/hr) | Dimethyl Ether STY* (g/l/hr) |
|---|---|---|---|---|
| Ferrierite | 2-D | 10, 8 | 301 | 498 |
| Mordenite | 1-D | 12, 8 | 45 | 64 |
| ZSM-5 | 3-D | 10 | 62 | 100 |

*based on (methanol converted + acetic acid produced)/2

EXAMPLE 10

This experiment was carried out to test the catalytic activity of ferrierite in the liquid phase production of acetic acid and dimethyl ether from a feed of methanol, methyl acetate water and acetic acid. The silica:alumina ratio of the ferrierite was 20 and contained 20 wt % alumina binder (based on total weight). The experiments were conducted on an X-Cube™ continuous flow reactor (ex ThalesNano Nanotechnology Incorporated). The reaction was carried out at a temperature of 170° C., a pressure of 50 barg, a liquid hourly space velocity of 2 hr$^{-1}$ and a feed containing 23.3 mol % methanol, 49.6 mol % methyl acetate, 26.4 mol % water and 0.7 mol % acetic acid. Liquid reaction product from the reactor was collected after 50, 100 and 200 hours on stream and analysed using gas chromatographs equipped with an open tubular silica column coated with CP-Poraplot Q and a TCD. The results of the experiment are given in Table 6 below.

TABLE 6

| Time on stream (hrs) | DME STY (g/l/hr) | Acetic Acid STY (g/l/hr) |
|---|---|---|
| 50 | 168 | 313 |
| 100 | 169 | 309 |
| 200 | 162 | 301 |

EXAMPLE 11

In this Example, the catalytic activities of H-Ferrierite, H-MCM-22 and H-Theta-1 were tested. The silica:alumina ratio for ferrierite was 17. Prior to use each zeolite was crushed and sieved to particle sizes in the range 250 to 500 microns.

Example 4 was repeated except that a temperature of 180° C. and a gas hourly space velocity of approximately 7600 h$^{-1}$ were maintained throughout the course of each reaction. The average space time yields (STY) to acetic acid and dimethyl ether for the period 150 to 170 hours on stream are given in Table 7 below.

TABLE 7

| Catalyst | Channel System | Ring Size | Framework Type | Acetic Acid STY (g/l/hr) | Dimethyl Ether STY* (g/l/hr) |
|---|---|---|---|---|---|
| Ferrierite | 2-D | 10, 8 | FER | 183 | 385 |
| MCM-22 | 2-D | 10, 6 | MWW | 58 | 103 |
| Theta-1 | 1-D | 10 | TON | 1 | 27 |

*based on (methanol converted + acetic acid produced)/2

EXAMPLE 12

In this Example, the catalytic activity of H-Ferrierite bound with 20% by weight alumina and a silica:alumina ratio of 20 was tested. Prior to use the zeolite was crushed and sieved to particle sizes in the range 250 to 500 microns.

Example 4 was repeated using 0.5 ml of ferrierite and a gas hourly space velocity of approximately 10,600 h$^{-1}$ was maintained throughout the course of the reaction. The reactor was initially adjusted to a temperature of 180° C. and maintained at this temperature for 90 hours. The temperature was then increased to 210° C. and the reaction was allowed to continue for a further 75 hours, after which time the temperature was increased to 240° C. and the reaction was allowed to continue for a further 100 hours. The average space time yields (STY) to acetic acid and dimethyl ether are given in Table 8 below.

TABLE 8

| Catalyst | Time Period (hrs) | Temp. (° C.) | Acetic Acid STY (g/l/hr) | Dimethyl Ether STY* (g/l/hr) |
|---|---|---|---|---|
| Ferrierite | 70-90 | 180 | 307 | 611 |
| Ferrierite | 130-150 | 210 | 522 | 724 |
| Ferrierite | 230-250 | 240 | 562 | 724 |

*based on (methanol converted + acetic acid produced)/2

EXAMPLE 13

In this Example, the catalytic activities of H-Ferrierite, H-Zeolite-Y and H-Clinoptilolite were tested. Ferrierite and Zeolite Y were each bound with 20% by weight of alumina (based on total weight) and had a silica:alumina ratio of 20 and 30 respectively. The clinoptilolite contained 1.2 wt % alkali metal. Prior to use each zeolite was crushed and sieved to particle sizes in the range 250 to 500 microns.

Example 4 was repeated except that a temperature of 180° C. and a gas hourly space velocity of approximately 10,600 $h^{-1}$ were maintained throughout the course of each reaction. The average space time yields (STY) to acetic acid and dimethyl ether are given in Table 9 below.

TABLE 9

| Catalyst | Channel System | Ring Size | Framework Type | Acetic Acid STY (g/l/hr) | Dimethyl Ether STY* (g/l/hr) |
|---|---|---|---|---|---|
| Ferrierite | 2-D | 10, 8 | FER | 283 | 592 |
| Clinoptilolite | 2-D | 10, 8 | HEU | 99 | 305 |
| Zeolite Y | 3-D | 12 | FAU | 56 | 17 |

*based on (methanol converted + acetic acid produced)/2

EXAMPLE 14

This experiment was carried out to test ferrierite for catalytic activity in the vapour phase production of acetic acid and dimethyl ether from methanol and methyl acetate. Ferrierite having a silica:alumina ratio of 20 and bound with 20% by weight of alumina was used as whole particle extrudates with a nominal diameter of 3.2 mm. 2 ml of the ferrierite, supported on a glass wool plug, was tested within a hastelloy tube reactor containing 50 ml of a silicon carbide pre-bed. A glass wool plug separated the ferrierite and the pre-bed. A vapour phase feed of 35 mol % methyl acetate, 21 mol % methanol, 14 mol % water and 30 mol % helium was introduced into the reactor and contacted the ferrierite at an initial temperature of 200° C., a pressure of 26 barg and a gas hourly space velocity (GHSV) of 21,400 $h^{-1}$. The reaction was allowed to continue for 5.5 hours before the GHSV was reduced to 10,700 $h^{-1}$. After a further 18 hours the GHSV was increased to 21,400 $h^{-1}$ and the temperature increased to 220° C. After 6 hours the GHSV was reduced to 10,700 $h^{-1}$. The reaction was allowed to continue for a further 18 hours after which time the GHSV was increased to 21,400 $h^{-1}$ and the temperature increased to 240° C. After 4 hours under these conditions, the GHSV was reduced to 10,700 $h^{-1}$ and the reaction was allowed to continue for another 21 hours. The gaseous product stream was analysed by gas chromatography. The liquid product stream was periodically collected in a pressurised vessel which was let-down to atmospheric pressure and the contents analysed by gas chromatography. The average space time yields (STY) to acetic acid and dimethyl ether are given in Table 10 below.

TABLE 10

| Catalyst | Temp. (° C.) | GHSV ($h^{-1}$) | Acetic Acid STY (g/l/hr) | Dimethyl Ether STY* (g/l/hr) |
|---|---|---|---|---|
| Ferrierite | 200 | 21400 | 1543 | 2954 |
| Ferrierite | 200 | 10700 | 1047 | 1769 |
| Ferrierite | 220 | 21400 | 2091 | 3262 |
| Ferrierite | 220 | 10700 | 1251 | 1685 |
| Ferrierite | 240 | 21400 | 2654 | 3544 |
| Ferrierite | 240 | 10700 | 1645 | 1866 |

*based on (methanol converted + acetic acid produced)/2

The invention claimed is:

1. A process for the production of acetic acid and dimethyl ether in which process methanol and methyl acetate are contacted with a catalyst composition in a reaction zone at a temperature in the range 140 to 250° C. to produce acetic acid and dimethyl ether and wherein said catalyst composition comprises a zeolite which has a 2-dimensional channel system comprising at least one channel having a 10-membered ring and at least one channel having an 8-membered ring.

2. A process according to claim 1 wherein the 2-dimensional channel system comprises inter-connecting channels.

3. A process according to claim 1 wherein the zeolite is selected from zeolites having framework structure types FER, HEU, MFS, DAC, STI, NES, MWW and TER.

4. A process according to claim 3 wherein the zeolite is selected from zeolites having a framework structure type FER, HEU and MFS.

5. A process according to claim 4 wherein the zeolite is selected from ferrierite, ZSM-35, ZSM-57 and clinoptilolite.

6. A process according to claim 1 wherein the zeolite is used in the acid form.

7. A process according to claim 1 wherein the zeolite has an alkali and alkaline earth metal content in a total amount in the range 0 to 0.2% by weight of the zeolite.

8. A process according to claim 1 wherein the zeolite has a silica : alumina ratio is in the range 5 to 90 : 1.

9. A process according to claim 8 wherein the silica : alumina ratio is in the range 15 to 60 : 1.

10. A process according to claim 1 wherein the catalyst composition comprises at least one inorganic oxide binder.

11. A process according to claim 10 wherein the binder is present in an amount in the range 10 wt % to 90 wt % (based on the total weight of zeolite and binder).

12. A process according to claim 1 wherein the molar ratio of methanol : methyl acetate is in the range 1:0.1 to 1:10.

13. A process according to claim 1 wherein the process is operated in the liquid or vapour phase.

14. A process according to claim 13 wherein the process is operated in the vapour phase at a temperature of 175 to 240° C.

15. A process according to claim 13 wherein the process is operated in the liquid phase at a temperature of 160 to 190° C.

16. A process according to claim 1 wherein water is added to the reaction zone.

17. A process according to claim 1 wherein the process is operated in the vapour phase at a temperature in the range 175 to 220° C., water is added to the reaction zone and wherein the zeolite is in the acid form.

18. A process according to claim 17 wherein the process is operated at a gas hourly space velocity (GHSV) in the range 2 to 25,000 $h^{-1}$.

19. A process according to claim 1 wherein the process is operated in the liquid phase at a temperature in the range 160 to 190° C., water is added to the reaction zone and wherein the zeolite is in the acid form.

20. A process according to claim 19 wherein the process is operated at a liquid hourly space velocity (LHSV) in the range 2 to 8 $h^-$.

21. A process according to claim 1 wherein the dimethyl ether produced is used as the feedstock to a process for the carbonylation of dimethyl ether.

* * * * *